United States Patent

Khachik et al.

[11] Patent Number: 5,386,063
[45] Date of Patent: Jan. 31, 1995

[54] SYNTHESIS OF (ALL-E)-2,7,-DIMETHYLOCTA-2,4,6-TRIENE-1,8-DIAL-$^{13}C_4$

[75] Inventors: Frederick Khachik, Beltsville; Gary R. Beecher, Laurel; Betty W. Li, Mitchellville, all of Md.

[73] Assignees: The Catholic University of America; The United States of America as represented by the Secretary of Agriculture, both of Washington, D.C.

[21] Appl. No.: 76,970

[22] Filed: Jun. 16, 1993

[51] Int. Cl.$^6$ .................. C07C 47/21; C07C 45/00
[52] U.S. Cl. .................. 568/494; 568/449; 568/484; 568/495

[58] Field of Search ............ 568/449, 494, 448, 484, 568/485, 495

[56] References Cited

U.S. PATENT DOCUMENTS 5,107,030  4/1992  Babler .................. 568/494

Primary Examiner—Werren B. Lone
Attorney, Agent, or Firm—Boris Haskell

[57] ABSTRACT (all-E)-2,7,-dimethylocta-2,4,6-triene-1,8-dial-$^{13}C_4$ is synthesized from commercially available and relatively inexpensive starting compounds, and the key starting compound is triethyl phosphonoacetate-$^{13}C_2$. The $^{13}C$ labeled dial is useful as an intermediate in synthesizing $^{13}C$ labeled carotenoids.

20 Claims, 2 Drawing Sheets 2,7-dimethylocta-2,4,6-triene-1,8-dial (VIII)
(C$_{10}$-Dialdehyde)

Wittig Salt (IX)

1,2-Epoxybutane
EtOH (Reflux)

(all-E,3R,3'R)-Zeaxanthin (X)

*C = $^{13}$C

5,386,063

SYNTHESIS OF (ALL-E)-2,7,-DIMETHYLOCTA-2,4,6-TRIENE-1,8-DIAL$^{13}$C$_4$

SUMMARY OF INVENTION

The present invention relates to an efficient and economical synthesis of:
(all-E)-2,7-dimethylocta-2,4,6-triene-1,8-dial-$^{13}$C$_4$ whose structural formula is shown as formula VIII in FIG. 1 of the drawings, and wherein C* designates $^{13}$C. In this specification, we will refer to this compound with its four $^{13}$C atoms as the C$_{10}$-dialdehyde.

In general, the purpose of the present invention is to enable the labeling of carotenoids with a stable isotope, such as $^{13}$C. The C$_{10}$-dialdehyde without the $^{13}$C isotope is a known key intermediate in the synthesis of carotenoids. However, the known avenues of synthesizing this compound do not permit the efficient and economical introduction of a stable labeling isotope, such as $^{13}$C. In accordance with the present invention, an avenue of synthesis of the C$_{10}$-dialdehyde is provided, which utilizes as a starting material, a compound that is relatively inexpensive and is commercially available with $^{13}$C atoms in the molecule.

The synthesis scheme of the present invention may be generally summarized as follows Trethyl phosphonoacetate-$^{13}$C$_2$ is the key starting compound of the present invention, and is readily and commercially available at reasonable cost. This compound is alkylated to triethyl-2-phosphonopropionate-$^{13}$C$_2$, which is then reacted with fumarylaldehyde and fumarylaldehyde dimethylacetal to produce (all-E)-2,7-dimethylocta-2,4,6-triene-1,8-diacid ethyl ester-$^{13}$C$_4$, i.e. the C$_{10}$-diester (or the diester corresponding to the C$_{10}$-dialdehyde). This C$_{10}$-diester is then reduced to the corresponding dialcohol, and then oxidized to the C$_{10}$-dialdehyde. Since the starting compound contains two $^{13}$C atoms per molecule and two molecules of the phosphonoproprionate compound are reacted with each molecule of the fumarylaldehyde compound, the final product of this synthesis contains four $^{13}$C atoms.

As stated, the ultimate intended purpose of the C$_{10}$-dialdehyde is as an intermediate in the preparation of carotenoids with an appropriate labeling $^{13}$C isotope content to facilitate the in vivo study of the carotenoids in the metabolic and other biological functions of humans and other animals. In the past decade numerous epidemiological studies have shown an inverse relationship between consumption of fruits and vegetables and the risk of several types of human cancers. Nutritional prevention of cancer is based upon the mechanism of action of various chemical components that are present in foods associated with reduced cancer risks. Carotenoids are one of the major classes of compounds abundant in fruits and vegetables whose metabolic functions other than vitamin A activity are not known. In previous studies we have demonstrated that as many as 50–60 carotenoids may be present in a typical diet consumed in the United States. In addition to seven previously known carotenoids in human plasma, recently we have isolated and characterized eleven new carotenoids in the extracts from the plasma of several subjects. Among these newly identified carotenoids, we have detected low levels of 3 ketocarotenoids that are absent in common fruits and vegetables. Based on their chemical structures, these ketocarotenoids appear to be the oxidation products of lutein and zeaxanthin which are two of the most prominent hydroxycarotenoids found in fruits, vegetables, and human plasma.

One of the hypotheses to explain the possible role of carotenoids as cancer preventive agents is based on the antioxidant capability of these compounds to quench singlet oxygen and other oxidizing species, inhibit lipid peroxidation and prevent the neoplastic cells from further promotion and replication. If a free radical mechanism is involved in the initiation and promotion of carcinogenesis, carotenoids such as lutein and zeaxanthin may participate in the quenching of the peroxides and the prevention of cellular oxidative damage. Therefore human feeding studies are required in order to investigate the absorption, bioavailability, and metabolism of carotenoids such as lutein and zeaxanthin.

In these human intervention studies, synthetic lutein and zeaxanthin labeled with the stable isotope $^{13}$C are needed to investigate the mechanism of an in vivo oxidation for these compounds. An understanding of the function and metabolism of carotenoids and their oxidation products will be a significant contribution to the field of human nutrition, and will enable scientists to investigate the possible role of these compounds in prevention of cancer.

In a typical human metabolic study, subjects are supplemented with carotenoids labeled with a stable isotope, and at various intervals blood samples are collected. The extracts from serum or plasma of the subjects is then examined by liquid chromatography/mass spectrometry to determine the qualitative and quantitative distribution of various carotenoids and their metabolites.

In human metabolic studies with carotenoids, where certain chemical transformations such as oxidation/reduction reactions are of particular interest, the location of the label is not crucial, as these chemical transformations do not result in fragmentation of these compounds into smaller molecules. Therefore, the labels introduced at any part of the molecule are preserved as the general skeleton of the carotenoid molecule remains unchanged throughout these metabolic reactions. An exception to this case is the metabolism of vitamin A active carotenoids such as α- and β-carotene, where these compounds may undergo random cleavage and fragmentation across the polyene chain and result in the formation of vitamin A as well as a number of apocarotenals. In the study of the metabolism of these compounds additional labeling of the carbons in the polyene chain may be necessary. However, it is important that at least four carbon atoms in the carotenoid molecule be labeled, because the oxidation/reduction reactions of hydroxycarotenoids, such as zeaxanthin and lutein, result in the formation of a number of metabolites whose molecular masses only change by 2 to 4 mass units (Dalton) in comparison with the molecular mass of their parent carotenoids. In human feeding studies, where subjects ingest $^{13}$C-carotenoids, the various carotenoid metabolites can be readily distinguished from one another by evaluating enrichment of the label in the plasma carotenoid profile as determined by liquid chromatography/mass spectrometry.

The introduction of the $^{13}$C isotope into a carotenoid molecule is accomplished easily and inexpensively, by utilizing the synthetic pathway of the present invention to produce the C$_{10}$-dialdehyde. This labeled C$_{10}$-dialdehyde is then employed in a known manner as a key intermediate for the synthesis of a number of carotenoids.

It is therefore one object of the present invention to provide for the synthesis of $C_{10}$-dialdehyde.

Another object of the present invention is to provide an efficient and inexpensive synthetic pathway for the production of $C_{10}$-dialdehye.

Another object of the present invention is to provide an efficient and inexpensive pathway for the synthesis of a $^{13}C$ labeled intermediate for the synthesis of $^{13}C$-carotenoids.

And still another object of the present invention is to provide for the synthesis of $^{13}C$ labeled carotenoids wherein the intermediate is $C_{10}$-dialdehyde.

Other objects and advantages of the present invention will become apparent to those skilled in the art from a consideration of the following detailed description of the invention had in conjunction with the accompanying drawings.

DETAILED DESCRIPTION

Figure 1:
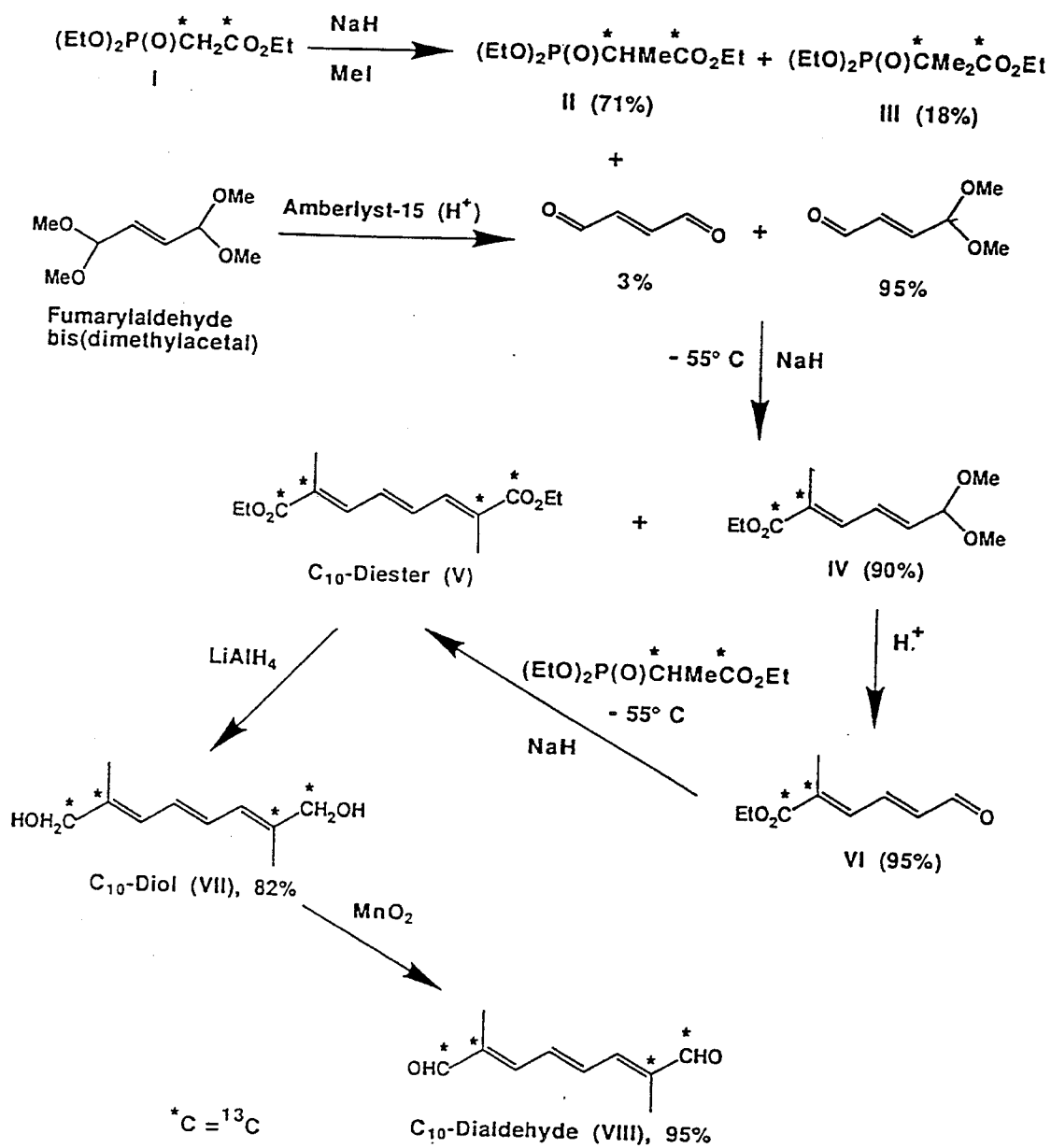
FIG. 1 depicts the synthesis pathway or scheme of the present invention for producing the $C_{10}$-dialdehyde.

The purpose of the present invention is to synthesize $^{13}C$ labeled $C_{10}$-dialdehyde efficiently and inexpensively. To that end, the primary starting compound and source of $^{13}C$ is trethyl phosphonoacetate-$^{13}C_2$, which is commercially available. This compound is depicted as formula I in the accompanying drawing. In the drawing, all $^{13}C$ atoms are represented by *C. The end product of the synthesis is (all-E) -2,7-dimethylocta-2,4,6,-triene-1,8-dial-$^{13}C_4$, referred to herein as $C_{10}$-dialdehyde, and depicted in the drawing as formula VIII. The entire scheme for the synthesis of $C_{10}$-dialdehyde is depicted in FIG. 1. Although each of the reactions employed in this synthesis is individually known, the overall synthesis of either labeled or unlabeled $C_{10}$-dialdehyde in the pathway depicted is novel.

The first step of this synthesis involves alkylation of trethyl phosphonoacetate-$^{13}C_2$ (I) with methyl iodide, resulting in a 71% yield of triethyl-2-phosphonopropionate-$^{13}C_2$ (the desired product, II), together with 18% of a side product identified as triethyl-2-methyl-2-phosphonopropionate-$^{13}C_2$ (III), and 11% of the unreacted starting material (I). The side product III does not interfere with the subsequent step of the synthesis. However, the unreacted starting material I, must be separated and removed from the mixture of products, and that may be done by flash column chromatography. The Wittig-Horner-Emmons reaction between compound II and a mixture of fumarylaldehyde (3%) and fumarylaldehyde dimethylacetal (95%), obtained by catalytic hydrolysis of fumarylaldehyde bis(dimethylacetal) according to G. M. Coppola, Synth. Commun. 1021–1023, 1984, results in the formation of ethyl 6,6-dimethoxy-2-methyl-E,E-2,4-hexadienoate$^{13}C_2$ (IV, 90%) and (all-E)-2,7-dimethylocta-2,4,6-triene-1,8-diacid ethyl ester-$^{13}C_4$ ($C_{10}$-diester, V, 3%). Compound IV, in the crude mixture with compound V, is hydrolyzed at room temperature to give 95% yield of ethyl 2-methyl-6-oxo-E,E-2,4-hexadienoate-$^{13}C_2$ (VI), while the $C_{10}$-diester V remains unchanged. The crude mixture of compounds V and VI is then treated with the sodium salt of compound II to give a 90% yield of compound V, which is purified by recrystallization. Reduction of compound V in the manner of published procedures for the unlabeled compound, according to H. H. Inhoffen et. al., Liebigs Ann. Chem. 132–139, 1954, provides an 82% yield of (all-E)-2,7-dimethylocta-2,4,6-triene-1,8-diol-$^{13}C_4$ ($C_{10}$-diol VII). Oxidation of compound VII with manganese dioxide according to the published methods for the unlabeled compound (id.) results in a 95% yield of the desired $C_{10}$-dialdehyde VIII. The overall yield of compound VIII based on compound II is 57–60%.

Alternatively, the direct synthesis of the $C_{10}$-diester (V) from a double Wittig-Horner-Emmons condensation of compound II with fumarylaldehyde resulted in poor yields (<30%). This is mainly due to the difficulties associated with preparation and purification of fumarylaldehyde (See D. L. Hufford et al., J. Am. Chem. Soc., 74, 3014–18, 1952.)

Figure 2:
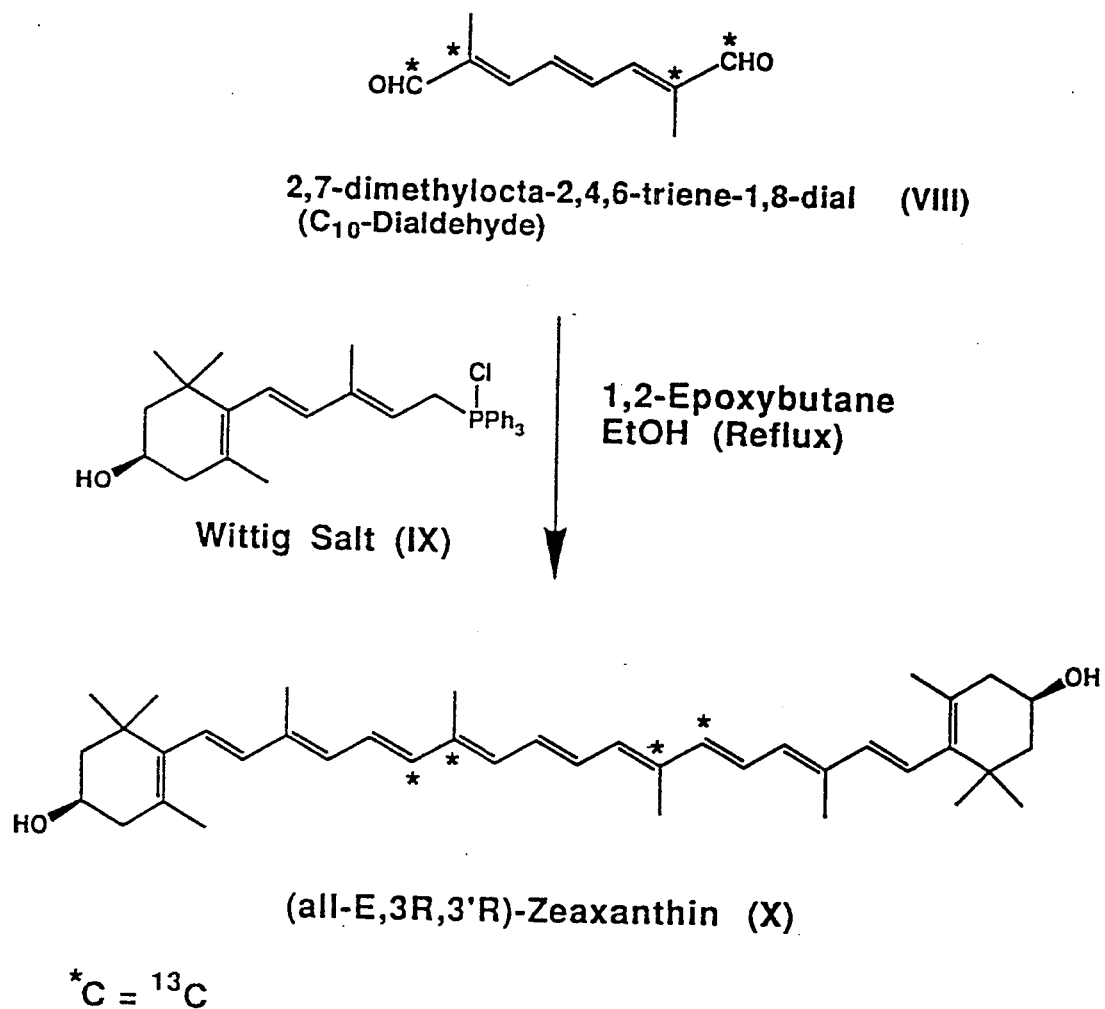
FIG. 2 depicts the use of the $C_{10}$-dialdehyde in the synthesis of a carotenoid, namely zeaxanthin.

The $C_{10}$-dialdehyde (VIII) has been employed in a double Wittig reaction with {(2E,4E)-5[(R)-4-hydroxy-2,6,6-trimethylcyclohex-1-enyl]-3-methylpenta-2,4-dienyl} triphenylphosphonium chloride (Wittig salt, IX) to synthesize (all-E,3R, 3'R)-zeaxanthin-$^{13}C_4$ (X) as shown in FIG. 2, with a 90% yield, according to the procedures for the unlabeled compound of E. Widmer et al., Helv. Chem. Acta, 73, 861–67, 1990, and M. Soukup et al., id., at 867–73. Thus the introduction of the $^{13}C$ label into the molecular structure of zeaxanthin has been accomplished by the introduction of the label into the $C_{10}$ dialdehyde. Furthermore, other $^{13}C$-labeled carotenoids such as lutein, lycopene, α-cryptoxanthin, β-cryptoxanthin, α-carotene, and β-carotene can be readily prepared from $C_{10}$-dialdehyde (VIII) as this compound has been employed as a key intermediate in the synthesis of unlabeled caroteniods. See E. Widmer, Pure and Appl. Chem., 57, 741–752, 1985.

In order to further illustrate the reactions of the present synthesis scheme, the following specific examples are provided. The key reagents for these examples, triethyl phosphonoacetate-$^{13}C_2$, fumarylaldehyde bis(dimethylacetal), and Amberlyst-15 (ion-exchange macroreticular resin) were obtained from Aldrich Chemical Co., Milwaukee, Wis. All reactions were carried out in a three-necked flask, equipped with a magnetic stirrer, condenser, thermometer, addition funnel, and a nitrogen inlet. The flask at the beginning of each reaction was thoroughly flushed with nitrogen to exclude air and was kept under nitrogen atmosphere throughout the course of each reaction.

Synthesis of Triethyl 2-Phosphonoproprionate-$^{13}C_2$ (II)

To a suspension of NaH (95%) [0.90 g 95%=0.86 g, 0.036 mol] in tetrahydrofuran (THF, 20 ml dried over Na) cooled at 10° C., triethyl phosphonoacetate-$^{13}C_2$(I)[8.0 g, 0,035 mol] in THF (20 ml) was added over 15 minutes. The reaction mixture was allowed to warm up to room temperature and stirred at this temperature for 2.5 h. The reaction mixture was cooled to −5° C. and methyl iodide (5.20 g, 0.037 mol) in THF (20 ml) was added at this temperature over 10 minutes. The cold bath was removed and the mixture was allowed to warm up to room temperature and stirred at this temperature for 1 h. The mixture was cooled in an ice-bath, and water (30 ml) was added and the product was partitioned between water (100 ml/salt) and methylene chloride (100 ml). The methylene chloride layer was removed and the water layer was washed with methylene chloride (2×50 ml). The organic layers were combined and dried over sodium sulfate. After evaporation, 8.62 g of a colorless oil was obtained. The crude oil was examined by gas chromatography/mass spectrometry (GC/MS) and was shown to consist of unreacted triethyl phosphonoacetate-$^{13}C_2$ (I, 11%), triethyl 2-phosphonopropionate-$^{13}C_2$ (II, 71%), and a side product identified as triethyl 2-methyl-2-phosphonopropionate-$^{13}C_2$ (III, 18%).

Separation of Triethyl 2-Phosphonopropionate-$^{13}C_2$ (II) from Unreacted Triethyl Phosphonoacetate-$^{13}C_2$ (I) by Flash Column Chromatography A flash chromatographic column (40 cm×4 cm) was packed with 80 g of n-silica gel (60–200 mesh, Baker Analyzed, average particle diameter (APD)∼63–200 μm, mean pore diameter ∼60 Å) which corresponded to the height of 27 cm for the packing using petroleum ether (PE)[b.p. 30°–60° C.]. 8.62 g of the mixture was loaded into the column using 5 ml of PE. The column was first eluted with 100 ml of PE and 200 ml of PE (90%)/ether (10%). No product was shown by GC/MS to have eluted from the column at this time. Then fractions were collected as follows:

| Fractions | Volume (ml) | Elution Solvents |
|---|---|---|
| 1–12 | 75 | PE 90%/ether 10% |
| 13–25 | 75 | PE 80%/ether 20% |
| 25–70 | 75 | PE 70%/ether 30% |
| 71–80 | 75 | PE 30%/ether 70% |

All of the fractions were monitored by GC/MS equipped with an autosampler to determine the purity of the desired product (II). Fractions 16–70 (7 g) were combined. The combined fractions were shown by GC/MS to consist of triethyl 2-phosphonopropionate-$^{13}C_2$ (II, 86%, 6 g) and triethyl 2-methyl-2-phosphonopropionate-$^{13}C_2$ (III, 14%, 1 g). Fractions 10, 11, 12(0.5 g) were shown to consist of the side product III and were combined. Fractions 71–80( 0.80 g) were combined and the mixture was shown by GC/MS to consist of compound I (90%) and compound II(10%).

Hydrolysis of Fumarylaldehyde bis (Dimethylacetal)

This compound was prepared according to the method of G. M. Coppola, Synth. Commun., 1021–1023, 1984. A solution of fumarylaldehyde bis(dimethylacetal) (10 g) was dissolved in 240 ml of THF in a three necked flask under an atmosphere of nitrogen. 3.6 ml of water was added followed by 2.4 g of Amberlyst-15 (dry) and the mixture was stirred at room temperature for 5 minutes. The product was filtered under vacuum in a flask containing sodium sulfate and the catalyst was washed with THF (120 ml). The solution was stirred with sodium sulfate and filtered off after 20 minutes. Most of the THF was evaporated on a rotary evaporator at 30° C. and the residue was distilled in vacuo at 72°–76° C. (10 mmHg) to give pure fumarylaldehyde dimethylacetal (6 g, 0.046 mole; 81%).

Synthesis of Ethyl 6,6-Dimethoxy-2-Methyl-E,E-2,4-Hexadienoate-$^{13}C_2$ (IV)

To a suspension of sodium hydride (95%) [0.36 g 95%=0.34 g, 0.014 mol] in THF (20 ml dried over Na) cooled at 10° C., triethyl 2-phosphonopropionate-$^{13}C_2$ (II) [3.4 g, 86% pure ∼2.92 g, 0.0122 mol, purified by flash column chromatography] in THF (15 ml) was added over 15 minutes. The reaction mixture was allowed to warm up to room temperature and stirred at this temperature for 2.5 h. Fumarylaldehyde dimethylacetal (1.82 g, 0.014 mol) in 30 ml of THF was added over 1.5 h. at −50° to −60° C. After the addition was completed, the reaction mixture was stirred at −50° C. for an additional hour. The mixture was allowed to warm up to room temperature and was then refluxed for 1 h. The product was cooled in an ice-bath, and water (30 ml) was added. The crude mixture was partitioned between methylene chloride (100 ml) and water (100 ml/salt). The methylene chloride layer was removed and the water layer was washed with methylene chloride (2×50 ml). The combined methylene chloride layers was dried over sodium sulfate and evaporated to dryness to give 6 g of crude oil, which was shown by UV/visible spectrophotometry and mass spectrometry to consist mainly of ethyl 6,6-dimethoxy-2-methyl-E,E-2,4-hexadienoate-$^{13}C_2$(IV) (2.37 g, 0.011 mol, 90%) and low levels of (all-E) -2,7-dimethylocta-2,4,6-triene-1,8-diacid ethyl ester-$^{13}C_2$(V) (0.032 g, 0.00013 mol).

Hydrolysis of Ethyl 6, 6-Dimethoxy2-Methyl-E, E-2, 4-Hexadienoate-$^{13}C_2$ (IV) to Ethyl 2-Methyl-6-Oxo-E, E-2,4-Hexadienoate-$^{13}C_2$ (VI)

The crude product from the previous reaction (total weight 6 g. containing 2.37 g of compound IV) was dissolved in 100 ml of THF and 10 ml of dilute sulfuric acid (from 1.80 ml of conc. sulfuric acid into 100 ml of water, saturated with sodium sulfate). After 1 h, the product was partitioned between methylene chloride (100 ml) and water (100 ml). The organic layer was removed, dried over sodium sulfate and evaporated to dryness to give 3.95 g of a crude product which was identified by high performance liquid chromatography/mass spectrometry and UV/visible absorption spectrophotometry as a mixture of ethyl 2-methyl-6-oxo-E,E-2,4-hexadienoate-$^{13}C_2$ (VI) [1.78 g, 0.0105 mol, 95%] and (all-E) -2,7-dimethylocta-2,4,6-triene-1,8-diacid ethyl ester-$^{13}C_4$ (V) [0.032 g, 0.00013 mol].

Synthesis of (all-E) -2,7Dimethylocta-2,4,6-Triene1,8-Diacid Ethyl Ester-$^{13}C_4$(V)

To a suspension of Nail (95%)[0.29 g 95%=0.28 g, 0.012 mol] in THF (15 ml dried over Na) cooled at 10° C., triethyl 2-phosphonopropionate-$^{13}C_2$ (3.14 g, 86% pure ∼2.70 g, 0.0112 mol) in 15 ml of THF was added over 15 minutes. The reaction mixture was allowed to warm up to room temperature and stirred at this temperature for 2.5 h. Ethyl 2-methyl-6-oxo-E,E-2,4-hexadienoate-$^{13}C_2$ (VI) [1.78 g, 0.0105 mol] in 20 ml of THF was added in 1.5 h. at −50° to −60° C. After the addition was completed, the reaction mixture was stirred at −50° C. for an additional hour and then allowed to warm up to room temperature. The mixture was refluxed for 1 h. The product was cooled in an ice-bath, and water (30 ml) was added. The crude mixture was partitioned between methylene chloride (100 ml) and water (100 ml/salt). The methylene chloride layer was removed and the water layer was washed with methylene chloride (2×50 ml). The combined methylene chloride layers was dried over sodium sulfate and evaporated to dryness to give a crude oil of 4.50 g which was recrystallized from ethyl alcohol to give (all-E)-2,7-dimethylocta-2,4,6-triene-1,8-diacid ethyl ester-$^{13}C_4$(V)[2.42 g, 0.0095 mol, ~90%], as determined by UV/visible spectrophotometry, mass spectrometry and nuclear magnetic resonance.

Synthesis of (all-E)-2,7Dimethylocta-2,4,6-Triene-1,8-Diol-$^{13}C_4$ (VII)

This synthesis was conducted in the same manner as the published method for the synthesis of the unlabelled compound VII (H. H. Inhoffen et al., Liebigs Ann, Chem., 132–139, 1954.) Lithium aluminum hydride (4.0 g) was heated at reflux in ether (280 ml) for 15 minutes. The decanted solution (160 ml) was transferred into a three necked flask and cooled to −15° C. (all-E)-2,7-dimethylocta-2,4,6-triene-1,8-diacid ethyl ester-$^{13}C_4$ (1.20 g, 0.00468 mol) was dissolved in ~5–10 minutes (so that the temperature did not rise above −10° C.). The mixture was stirred for 15 minutes at −15° C. At this point UV/visible spectrophotometry indicated the end of the reaction [$\lambda_{max}$ of product in ether=281 nm]. Methanol (30 ml) was added slowly at −20° C., until the excess lithium aluminum hydride was destroyed. This was followed by the addition of a saturated solution of ammonium chloride (200 ml). The product was extracted into ether and the water layer was washed with ether (3×150 ml). The combined ether layers was evaporated to dryness to give ~0.90 g of a white solid identified by its UV/visible absorption spectrum and mass spectrum, and by nuclear magnetic resonance, as (all-E)-2,7-dimethylocta-2,4,6-triene-1,8-diol-$^{13}C_4$ (VII) [~0.66 g pure, 0.0038 mol, 82% ].

Synthesis of (all-E)-2,7-Dimethylocta-2,4,6-Triene-1,8-Dial-$^{13}C_4$ (VIII)

This synthesis was conducted in the same manner as the published synthesis of the unlabeled VIII. (H. H. Inhoffen et al., cited in the preceding synthesis.) The crude diol VII (0.66 g, 0038 mol) was dissolved in acetone (600 ml), and activated manganese dioxide (17.5 g) was added. The mixture was stirred in vacuo for 3 h. The solution (pale yellow) was filtered through celite and evaporated to dryness to give a yellowish crude residue (0.60 g). This was dissolved in ~15 ml of methylene chloride and microfiltered. Evaporation of solvent gave the pale yellow crystals of (all-E)-2,7-dimethylocta-2,4,6-triene-1,8-dial-$^{13}C_4$ (VIII), which was recrystallized from methylene chloride/ether to give pure compound VIII (0.61 g, 0.0036 mol, 95%). Compound VIII was identified and shown to be pure by high performance liquid chromatography/mass spectrometry, UV/visible absorption spectrophotometry, and nuclear magnetic resonance.

Preparation of (all-E,3R, 3′R)-Zeaxanthin-$^{13}C_4$ (X)

This synthesis was conducted in the same manner as the published synthesis for the unlabeled compound X, by E. Widmer et al., Helv. Chim. Acta, 73, 861–67, 1990. A solution of {(2E,4E)-5-[(R)-4-hydroxy-2,6,6-trimethylcyclohex-l-enyl]-3-methylpenta-2,4-dienyl} triphenylphosphonium chloride (Wittig salt IX) [1.034 g, 0.002 mol], (all-E)-2,7-dimethylocta-2,4,6-triene-1,8-dial-$^{13}C_4$ (VIII) [0.168 g, 0.001 mol] and 1,2-epoxybutane(0.60 g, 0.008 mol) in ethanol (10 ml) was stirred at reflux for 20 h. The suspension was cooled to −10° C. and the product was filtered, washed with ethanol (10 ml, −15° C.), and recrystallized from methylene chloride, containing 1% triethyl amine and hexane and dried at 60° C./0.1 mm for 3 days. This gave pure (all-E, 3R, 3′R)-zeaxanthin-$^{13}C_4$(X)[0.52 g, 0.0009 mol, 90%]. The product X was shown by high performance liquid chromatography to consist of more than 99% (all-E)-isomer.

Direct Synthesis of (all-E)-2,7-Dimethyl-2,4, 6-Triene-1,8-Diacid Ethyl Ester-$^{13}C_4$ (V)

A suspension of sodium hydride (95%)[0.18 g 95%=0.17 g, 0.007 mol] in THF (10 ml) in a three-necked flask equipped with a magnetic stirrer, dry-ice condenser, addition funnel equipped with dry/ice jacket, low temperature thermometer, and a nitrogen inlet, was cooled to 10° C. Triethyl 2-phosphonopropionate$^{13}C_2$ (II) [1.7 g, 86% pure ~1.5 g, 0.0063 mol, purified by flash column chromatography] in THF (7 ml) was added over 15 minutes. The reaction mixture was cooled to −60° C. (dry-ice/acetone) and fumaric dialdehyde (0.27 g, 0.0032 mol) [prepared according to the method of Hufford et al., J. Am. Chem. Soc., 74, 3014–18, 1952] in THF (30 ml) cooled in the addition funnel to −60° C. was added slowly over 3 h. The dry-ice bath was removed and the reaction mixture was allowed to warm up to room temperature and stirring continued at this temperature for 2 h. Water (15 ml) was added and the crude mixture was partitioned between methylene chloride (50 ml) and water (50 ml/salt). The methylene chloride layer was removed and the water layer was washed with methylene chloride (2×25 ml). The combined methylene chloride layers was dried over sodium sulfate and evaporated to dryness to give a dark brown residue (2.3 g). The yield of the product V in the crude mixture based on UV/visible spectrophotometric analysis was ~20%.

In the foregoing description, the present invention has been described in detail with illustrative procedures for implementing it. However, the scope of the invention is not limited to the stated detailed description thereof, and such variations and modifications as are embraced by the spirit and scope of the appended claims are contemplated as being within the scope of this invention.

We claim:

1. A method of producing (all-E)-2,7-dimethylocta-2,4,6-triene-1,8-dial comprising the steps of reacting triethyl-2-phosphonopropionate with fumarylaldehyde and/or fumaryaldehyde dimethylacetal to produce (all-E)-2,7 dimethylocta-2,4,6-triene-1,8-diacid ethyl ester, and converting the diester to said dialdehyde.

2. A method as set forth in claim 1, wherein said phosphonopropionate contains a $^{13}C$ atom, and said dialdehyde contains $^{13}C$ atoms.

3. A method as set forth in claim 2, wherein said phosphonopropionate contains two $^{13}C$ atoms and said dialdehyde contains four $^{13}C$ atoms.

4. A method as set forth in claim 1 wherein said phosphonopropionate is formed by alkylation of trethyl phosphonoacetate.

5. A method as set forth in claim 4, wherein said trethyl phosphonoacetate contains a $^{13}C$ atom.

6. A method as set forth in claim 5, wherein said trethyl phosphonoacetate contains two $^{13}C$ atoms.

7. A method of producing (all-E)-2,7-dimethylocta-2,4,6-triene-1,8-dial comprising the steps of alkylation of trethyl phosphonoacetate to produce triethyl-2-phosphonopropionate, hydrolyzing fumarylaldehyde bis(-dimethylacetal) to a mixture of fumarylaldehyde and fumarylaldehyde dimethylacetal, reacting said mixture with said phosphonopropionate to form ethyl 6,6-dimethoxy-2-methyl-E,E-2,4-hexadienoate and (all-E) -2,7 dimethylocta-2,4,6-triene-1,8-diacid ethyl ester, hydrolyzing the hexadieneoate to ethyl 2-methyl-6-oxo-E,E-2,4-hexadienoate and reacting said oxo-hexadienoate with the salt of triethyl-2-phosphonopropionate to produce (all-E) -2,7-dimethylocta-2,4,6-triene-1,8-diacid ethyl ester, reducing the diester to the corresponding diol, and oxidizing the diol to said dial.

8. A method as set forth in claim 7, wherein said phosphonoacetate contains a $^{13}C$ atom.

9. A method as set forth in claim 8, wherein said phosphonoacetate contains two $^{13}C$ atoms.

10. A method as set forth in claim 7, wherein said dial contains $^{13}C$ atoms.

11. A method as set forth in claim 10, wherein said dial contains four $^{13}C$ atoms.

12. A method of producing (all-E)-2,7 dimethylocta-2,4,6-triene-1,8-dial comprising, reacting triethyl-2-phosphonopropionate with fumarylaldehyde dimethylacetal in a Wittig-Horner-Emmons reaction, hydrolyzing the product and further reacting the hydrolyzed product with triethyl-2-phosphonopropionate, to produce (all-E)-2,7-dimethylocta-2,4,6-triene-1,8-diacid ethyl ester, reducing the diester to the diol, and oxidizing the diol to said dial.

13. A method as set forth in claim 12, wherein said phosphonopropionate contains a $^{13}C$ atom.

14. A method as set forth in claim 13, wherein said phosphonopropionate contains two $^{13}C$ atoms.

15. A method as set forth in claim 13, wherein said dial contains $^{13}C$ atoms.

16. A method as set forth in claim 15, wherein said dial contains four $^{13}C$ atoms.

17. A method as set forth in claim 12, and further comprising reacting said dial with Wittig salt to produce (all-E,3R, 3'R)-Zeaxanthin.

18. A method as set forth in claim 17, wherein said dial contains a $^{13}C$ atom.

19. A method as set forth in claim 18, wherein said dial contains four $^{13}C$ atoms.

20. The method comprising reacting a phosphonoalkylacid ester with an aldehyde to substitute the alkylacid ester group for the aldehyde oxygen atom, and further converting said substituted alkylacid ester group to an alkyl aidehyde, wherein said alkylacid ester contains one or more $^{13}C$ atoms.

* * * * *